United States Patent [19]

Hosoda

[11] 4,384,775
[45] May 24, 1983

[54] LIGHT SUPPLY DEVICE FOR AN ENDOSCOPE

[75] Inventor: Seiichi Hosoda, Fuchu, Japan
[73] Assignee: Olympus Optical Co., Ltd., Tokyo, Japan
[21] Appl. No.: 244,806
[22] Filed: Mar. 17, 1981
[30] Foreign Application Priority Data
Mar. 19, 1980 [JP] Japan .................................. 55-34984
[51] Int. Cl.³ .......................... G03B 29/00; A61B 1/06
[52] U.S. Cl. ........................................... 354/62; 128/6
[58] Field of Search ............................... 354/62; 128/6

[56] References Cited
U.S. PATENT DOCUMENTS

| | | | |
|---|---|---|---|
| 3,599,630 | 8/1971 | Sato et al. | 354/62 |
| 3,742,947 | 7/1973 | Hashem. | |
| 4,153,356 | 5/1979 | Hama | 354/62 |
| 4,281,910 | 8/1981 | Takayama | 354/62 |
| 4,284,338 | 8/1981 | Ikuno | 354/62 |
| 4,298,260 | 11/1981 | Takayama | 354/62 |

FOREIGN PATENT DOCUMENTS

50-108798 8/1975 Japan .

*Primary Examiner*—Russell E. Adams
*Attorney, Agent, or Firm*—Frishauf, Holtz, Goodman & Woodward

[57] ABSTRACT

An endoscope is connected to a light supply device through a universal cord. The light supply device includes an illumination lamp for emitting a diagnostic light and a stroboscopic tube for emitting a photographic light. The diagnostic light and photographic light are selectively conducted to the endoscope. A control section for controlling the operation of the flash tube includes a patient circuit, an intermediate circuit and a primary circuit. Optoisolators are provided to connect the intermediate circuit to the patient circuit as well as to the primary circuit while electrically isolating the intermediate circuit from the patient circuit and from the primary circuit.

14 Claims, 6 Drawing Figures

LIGHT SUPPLY DEVICE FOR AN ENDOSCOPE

BACKGROUND OF THE INVENTION

This invention relates to a light supply device for an endoscope, and more particularly to a light supply device which supplies an endoscope with a light of desired intensity and has a prescribed insulation withstand voltage property.

An endoscope light supply device is generally included in medical electric equipment. Therefore, an endoscope light supply device should meet an item included in the safety regulations of various countries as well as those of international scope (e.g. UL, IEC, etc.), namely, a specification related to the insulation withstand voltage. This insulation withstand voltage specification prescribes that the abovementioned endoscope light supply device needs to be provided with an insulation withstand voltage property of at least 5,000 volts.

The conventional endoscope light supply device comprises a patient circuit connected to an endoscope to be introduced into a patient's coeliac cavity and a primary circuit directly connected to a commercial A.C. power source. A flash tube for emitting a light to photograph an affected portion of the patient's coeliac cavity is connected to the primary circuit, and actuated in response to a signal transmitted from the patient circuit. Further, to assure the aforesaid insulation withstand voltage property, the patient circuit and primary circuit are optically connected together and yet electrically isolated by means of an optoisolator.

With the prior art endoscope light supply device, however, the optoisolator for connecting the patient circuit to the primary circuit has a low withstand voltage. Where, therefore, a high voltage of, for example, 5,000 volts is impressed between the patient circuit and primary circuit, the optoisolation is very likely to be destroyed. Viewed this way, the conventional endoscope light supply device has the drawbacks that it does not fully meet the insulation withstand voltage specification included in the international safety regulations, and can not be regarded as completely safe for the patient, for example.

A pulse transformer acting as magnetic coupling means which might replace the optoisolator still has the drawbacks that the pulse transformer having a large size unavoidably renders an endoscope light supply device bulky; leads to an increase in the production cost of the above-mentioned device; and is unadapted to be used with an endoscope light supply device demanded to quickly process a signal, because the pulse transformer transmits a signal at a slower rate than the optoisolator.

It is accordingly the object of this invention to provide a light supply device for an endoscope which is quickly actuated and which is extremely safe for the human body.

SUMMARY OF THE INVENTION

To attain the above-mentioned object, this invention provides an endoscope light supply device which comprises a first circuit to be connected to the endoscope, a second circuit to be connected to a commercial A.C. power source, and a signal transfer means having a plurality of stages of optical coupling means provided between the first circuit and the second circuit for electrically insulating the first and second circuits from each other and transferring signals between the first and second circuits.

This invention can be more fully understood from the following detailed description when taken in conjunction with the accompanying drawings.

DETAILED DESCRIPTION

With an endoscope light supply device (FIGS. 1 to 3) according to a first embodiment of this invention, an endoscope 10 includes an insertion section 12, control section 14 and eyepiece section 16. The insertion section 12 is formed of a flexible tube for introduction into the coeliac cavity of the human body. The control section 14 is connected to a light supply device 20 through a universal cord 18. A light guide 22 formed of an optical fiber bundle extends through the insertion section 12, control section 14 and universal cord 18. One end portion of the light guide 22 is disposed at the open end of the control section 12. The other end portion 24 of the light guide 22 is inserted into the light supply device 20. An image guide 26 also formed of an optical fiber bundle extends through the insertion section 12 and control section 14. An object lens 28 is set close to the distal end of the insertion section 12, that is, the distal end of the image guide 26. A beam splitter 30 formed of a rectangular prism is provided in the eyepiece section 16 close to the proximal end of the image guide 26. An optoelectric transducing element 31 and eyepiece 32 are set adjacent to the beam splitter 30. A light beam conducted through the image guide 26 is diverted in two directions by the beam splitter 30. One portion of the light beam is delivered to the optoelectric transducing element 31. The other portion of the light beam is sent to the eyepiece 32. An endoscope camera 34 is detachably fitted to the eyepiece section 16. A photographic film 36, shutter 38, and synchronizing contact switch 40 are received in the endoscope camera 34. Reference numeral 42 denotes the surface of, for example, a patient's coeliac cavity.

Figure 1:
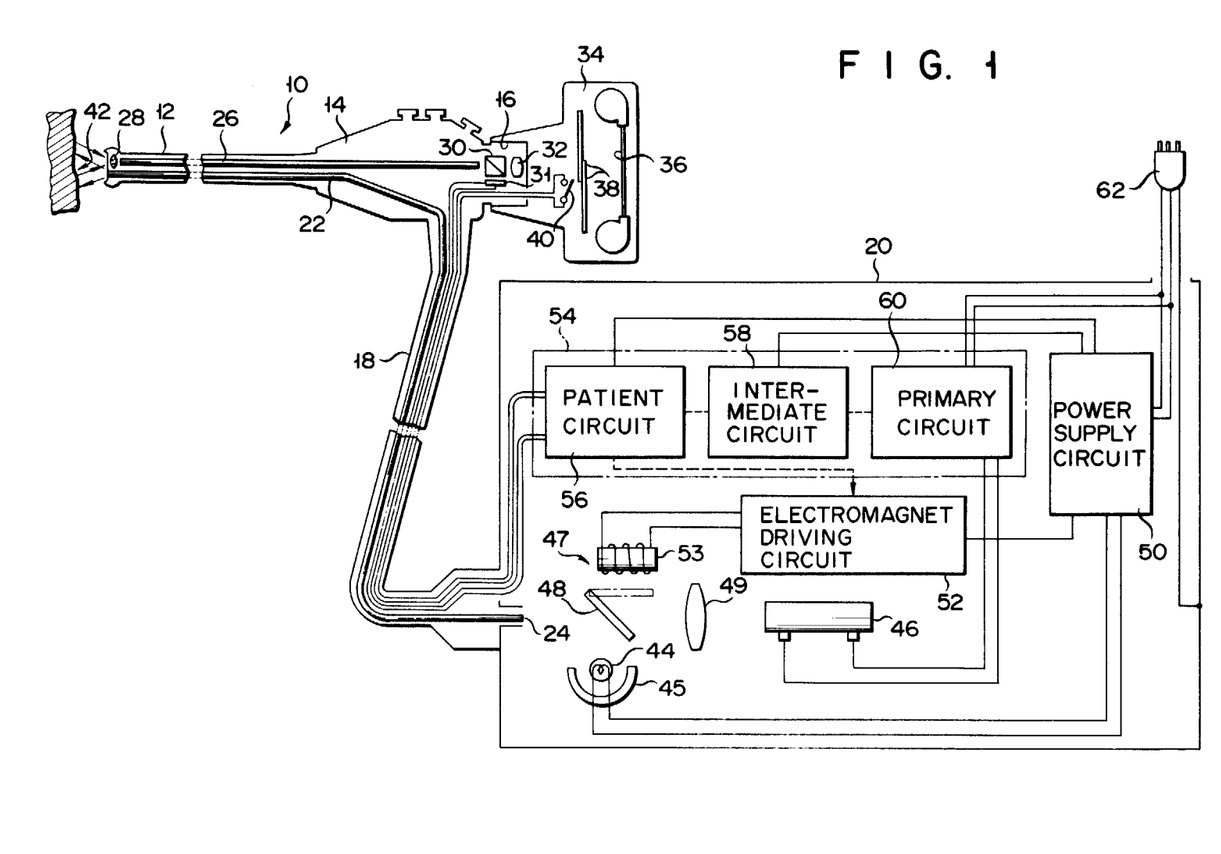
FIG. 1 is a schematic block circuit diagram showing the manner in which a first embodiment of a light supply device embodying this invention is connected to an endoscope.

The endoscope light supply device 20 comprises an illumination lamp 44 for emitting an observation light having a prescribed quantum, a reflection mirror 45 and a flash tube 46 for irradiating a photographic light having a larger quantum than the observation light. The observation light and photographic light are selectively transmitted to the endoscope 10 by a light-transmitting section 47. A light path-switching mirror 48 and light-condensing lens 49 (simply referred to as "a condenser") are provided between the proximal end 24 of the light guide 22 and flash tube 46. The illumination lamp 44 is connected to the first output terminals of a power supply circuit 50. The second output terminal of the power supply circuit 50 is connected to a solenoid or an electromagnet 53 through an electromagnet driving circuit 52. The electromagnet 53 is disposed near the light path-switching mirror 48. The light path-switching mirror 48 is normally inclined at an angle of, for example, 45° at a point facing the proximal end 24 of the light guide 22, so that an observation light emitted from the illumination lamp 44 can be directed to the proximal end of the light guide 22. Where, at the time of photographing, the electromagnet 53 is energized through the electromagnet driving circuit 52, then the light path-switching mirror 48 is lifted to cause a photographic light emitted from the flash tube 46 to be transmitted straight to the proximal end 24 of the light guide 22 through the condenser 49.

The control section 54 includes a patient circuit 56, intermediate circuit 58 and primary circuit 60. The first input terminals of the patient circuit 56 are connected to the optoelectric transducing element 31 held in the eyepiece section 16 of the endoscope 10 through the universal cord 18. The second input terminals of the patient circuit 56 are connected to the synchronizing contact switch 40 of the endoscope camera 34 similarly through the universal cord 18. An area defined between the output terminal of the patient circuit 56 and the input terminal of the intermediate circuit 58 and an area defined between the output terminal of the intermediate circuit 58 and the input terminal of the primary circuit 60 are electrically isolated and yet optically connected by means of, for example, the latter described optoisolator. One output terminal of the primary circuit 60 is optically connected to the other input terminal of the electromagnet driving circuit 52 by means of the later described optoisolator. The other output terminals of the primary circuit 60 are connected to the flash tube 46. The third input terminal of the patient circuit 56 and the other input terminal of the intermediate circuit 58 are respectively connected to the third and fourth output terminals of the power supply circuit 50. An input terminal of the power supply circuit 50 and an input terminal of the primary circuit 60 are connected to a commercial A.C. power source (not shown) through a cord plug 62. Additionally, one terminal of the cord plug 62 is connected to a metal housing of the light supply device 20.

Figure 2:
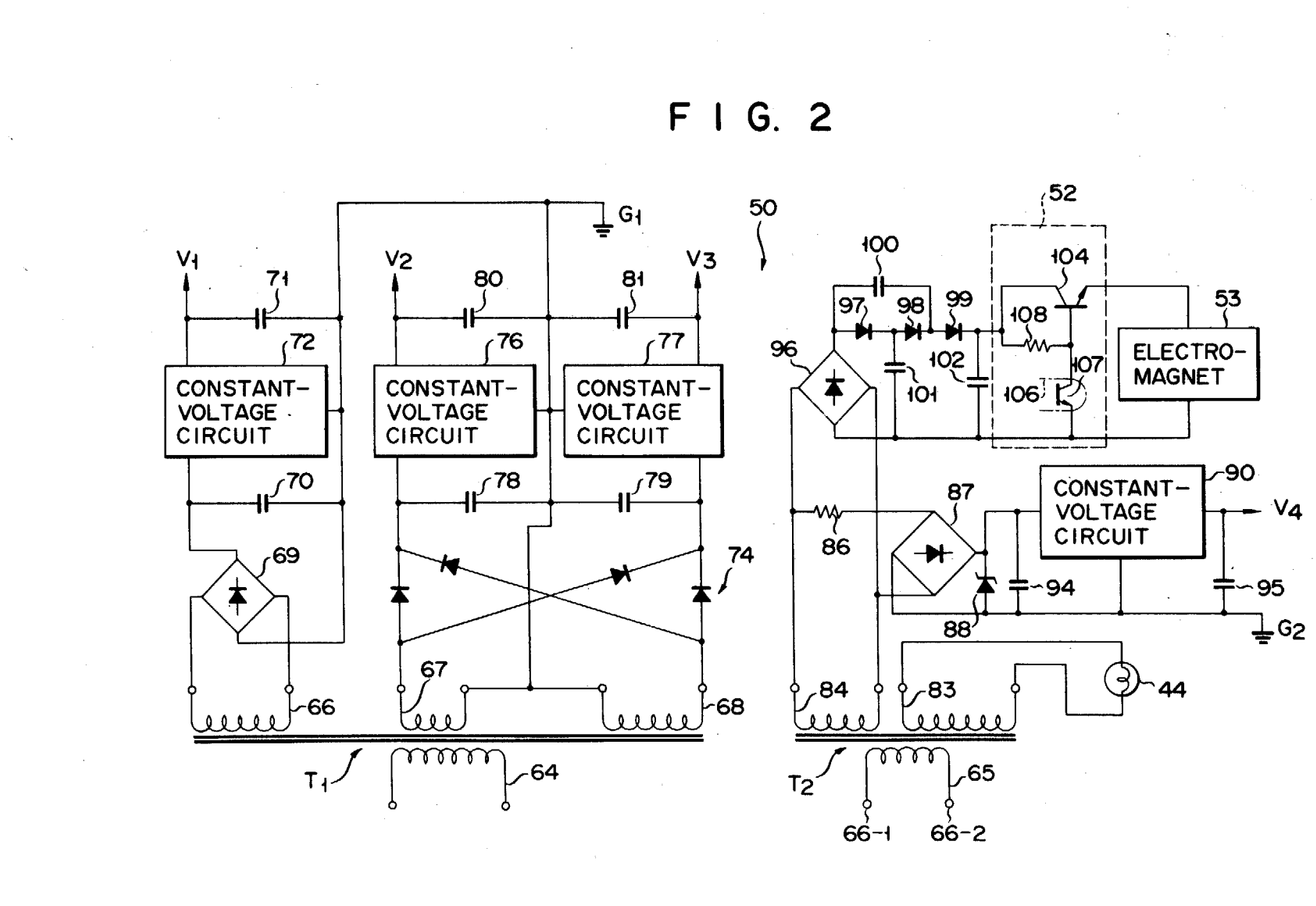
FIG. 2 schematically indicates the arrangement of a power supply circuit set in an endoscope light supply device.

As seen from FIG. 2, the power supply circuit 50 is arranged with a first transformer $T_1$ for supplying electric power on the patient circuit 56 and a second transformer $T_2$ for supplying electric power on the intermediate circuit 58. The primary windings 64, 65 of the first and second transformers $T_1$, $T_2$ are connected to the cord plug 62 (FIG. 1) in mutually parallel relationship. The first transformer $T_1$ includes secondary windings 66, 67, 68. The secondary winding 66 is connected to the input terminal of a full-wave rectifier 69. The output terminal of the full-wave rectifier 69 is connected to a smoothing capacitor 70, a bypass capacitor 71, and known voltage regulated circuit (hereinafter referred to as "a constant voltage circuit") 72. Accordingly, an output voltage $V_1$ of +5 volts is produced at one terminal of the constant voltage circuit 72. The other terminal of the full-wave rectifier 69 is grounded to earth indicated by $G_1$. The other secondary windings 67, 68 of the first transformer $T_1$ are connected to known full-wave rectifier 74 formed of four diodes, known constant voltage circuits 76, 77, smoothing capacitors 78, 79, and bypass capacitors 80, 81. The secondary windings 67, 68 are jointly grounded to the earth $G_1$. Accordingly, an output voltage $V_2$ of +15 V and an output voltage $V_3$ of −15 V are respectively produced at the output terminals of the constant voltage circuits 76, 77.

The second transformer $T_2$ includes secondary windings 83, 84. The secondary winding 83 is connected to the illumination lamp 44. The secondary winding 84 is connected to the input terminals of a full-wave rectifier 87 through a resistor 86. A zener diode 88, known constant voltage circuit 90, a smoothing capacitor 94, and a bypass capacitor 95 are connected to the output terminal of the full-wave rectifier 87. Accordingly, an output voltage $V_4$ of +5 V is produced at one output terminal of the constant voltage circuit 90. The other output terminal of the full-wave rectifier 87 is grounded to the other earth $G_2$ which is electrically separated from the earth $G_1$. The secondary winding 84 is also connected to the input terminal of another full-wave rectifier 96 connected in parallel with the full-wave rectifier 87. The output terminal of the full-wave rectifier 96 is connected to three diodes 97, 98, 99 and three capacitors 100, 101, 102 in the known manner. As a result, a triple rectified voltage is generated across the capacitor 102. The electromagnet driving circuit 52 is arranged with a series circuit consisting of an NPN type transistor 104 and the phototransistor 107 included in the later described optoisolator 106. This optoisolator 106 is connected between the patient circuit 56 and the NPN type transistor 104. The collector of the transistor 104 is connected to one terminal of the capacitor 102 at which a triple rectified voltage is produced. A phototransistor 107 is connected between the base of the transistor 104 and the other end of the capacitor 102. A resistor 108 is connected between the collector and base of the transistor 104. The above-mentioned electromagnet 53 is connected between the emitter of the transistor 104 and phototransistor 107.

Figure 3:
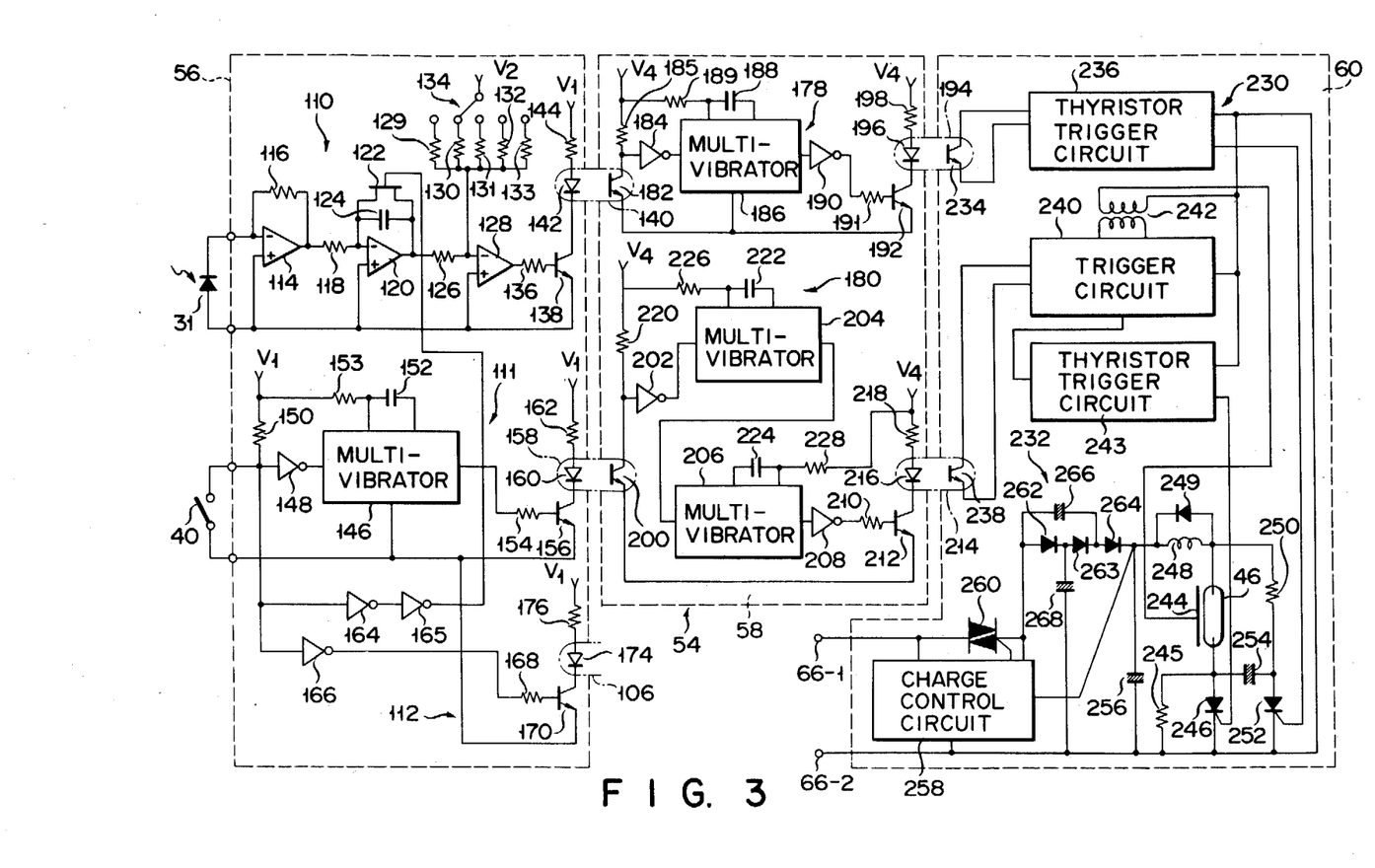
FIG. 3 sets forth the arrangement of an electric circuit of a control section provided in the endoscope light supply device of FIG. 1.

Referring now to the control section 54 shown in detail in FIG. 3, the patient circuit 56 includes an exposure control circuit 110 connected to the optoelectric element 31 set in the endoscope 10, flash synchronize circuit 111 connected to the synchronizing contact switch 40 and electromagnet signal-generating circuit 112. With the exposure control circuit 110, the input terminals of an operation amplifier 114 are connected to the optoelectric transducing element 31. The operation amplifier 114 converts an output current from the optoelectric transducing element 31 into a voltage signal. A resistor 116 is connected between a minus terminal of the input terminals and the output terminal of the operation amplifier 114. The output terminal is connected to one of the input terminals (a minus terminal) of an integrator 120 formed of an operation amplifier through another resistor 118. The other input terminal (a plus terminal) of the integrator 120 is connected to the other input terminal (a plus terminal) of the operation amplifier 114. An integration-starting FET 122 and integration capacitor 124 are connected in mutual parallel relationship between the minus terminal of the integrator 120 to which the resistor 118 is connected and the output terminal of the integrator 120. The output terminal of the integrator 120 is connected to one of the input terminals (a minus terminal) of a comparator 128 through a resistor 126. For example, five resistors 129, 130, 131, 132, 133 are connected to the minus input terminal of the comparator 128 mutually parallel relationship. These resistors are connected at one end to a changeover switch 134, whose input terminal is impressed with an output voltage $V_2$ from the power supply circuit 50. The other input terminal (a plus terminal) of the comparator 128 is directly connected to the other input terminal (the plus input terminal) of the integrator 120. The threshold voltage level of the comparator 128 is defined by the changeover switch 134 in accordance with, for example, the sensitivity of the film 36 of the endoscope camera 34, etc. The output terminal of the compartor 128 is connected to the base of an NPN transistor 138 through a resistor 136. The emitter of the transistor 138 is connected to the plus input terminal of the comparator 128. The collector of the transistor 138 is connected to the cathode of a light-emitting diode 142 of an optoisolator 140 which is provided between the patient circuit 57 and intermediate circuit 58. The anode of the light-emitting diode 142 is supplied with an output voltage $V_1$ from the power supply circuit 50 (FIG. 2) through a resistor 144.

The flash synchronize circuit 111 operated by the closure of the synchronizing contact switch 40 and electromagnet signal-generating circuit 112 cause one of the input terminals of a chattering-preventing one-shot multivibrator 146 to be connected to one of the terminals of the synchronizing contact switch 40 through an inverter 148. The one terminal of the synchronizing contact switch 40 is impressed with an output voltage $V_1$ from the power supply circuit 50 (FIG. 2) through a resistor 150. A capacitor 152 is connected in parallel to the multivibrator 146. One of the terminals of the capacitor 152 is impressed with an output voltage $V_1$ from the power supply circuit 50 through a resistor 153. The output terminal of the multivibrator 146 is connected to the base of an NPN transistor 156 through a resistor 154. The emitter of the transistor 156 is directly connected to the other terminal of the synchronizing contact switch 40 and multivibrator 146. The collector of the transistor 156 is connected to the cathode of a light-emitting diode 160 of an optoisolator 158 which is also provided between the patient circuit 56 and the intermediate circuit 58. The anode of the light-emitting diode 160 is impressed with an output voltage $V_1$ from the power supply circuit 50 through a resistor 162. The junction of the inverter 148 and resistor 150 is connected to the gate of the aforesaid FET 122 through two inverters 164, 165. Where an output signal from the synchronizing contact switch 40 is transmitted to the FET 122 through the inverters 164, 165, then the FET 122 is rendered nonconducting. At this time, the integrator 120 commences the integration of an output voltage from the optoelectric transducing element 31. The junction of the inverter 164 and resistor 150 is connected to the base of an NPN transistor 170 through the other inverter 166 and resistor 168. The emitter of the NPN transistor 170 is connected to the emitter of the aforementioned transistor 156. The collector of the NPN transistor 170 is connected to the cathode of a light-emitting diode 174 of the optoisolator 106. The anode of the light-emitting diode 174 is impressed with an output voltage $V_1$ from the power supply circuit 50 (FIG. 2).

The intermediate circuit 58 of the control section 54 includes a first transmission circuit 178 for transmitting an output light signal from the light-emitting diode 142 of the optoisolator 140 of the patient circuit 56 to the succeeding section and a second transmission circuit 180 for transmitting an output light signal from the light-emitting diode 160 of the optoisolator 158. The first transmission circuit 178 comprises a phototransistor 182 set in the optoisolator 140 in a state facing the light-emitting diode 142. The collector of the phototransistor 182 is connected to the input terminals of a one-shot multivibrator 186 through an inverter 184, and impressed with an output voltage $V_4$ from the power supply circuit 50 through a resistor 185. A capacitor 188 is connected in parallel to the one-shot multivibrator 186. One terminal of the capacitor 188 is similarly impressed with an output voltage $V_4$ from the power supply circuit 50 through a resistor 189. The output terminal of the multivibrator 186 is connected to the base of an NPN transistor 192 through an inverter 190 and resistor 191. The emitter of the NPN transistor 192 is connected to the emitter of the phototransistor 182 and one terminal of the multivibrator 186. The collector of the transistor 192 is connected to the cathode of a light-emitting diode 196 of an optoisolator 194 which is provided between the intermediate circuit 58 and the primary circuit 60. The anode of the transistor 192 is impressed with an output voltage $V_4$ from the power supply circuit 50 through a resistor 198.

The multivibrator 186 is actuated upon receipt of an output signal from the phototransistor 182 to generate a pulse signal for actuating the optoisolator 194.

The second transmission circuit 180 includes a phototransistor 200 provided in the optoisolator 158 in a state facing the light-emitting diode 160. The collector of the phototransistor 200 is connected to the base of an NPN transistor 212 through an inverter 202, two multivibrators 204, 206, inverter 208 and resistor 210. The emitter of the NPN transistor 212 is directly connected to the emitter of the phototransistor 200. The collector of the NPN transistor 212 is connected to the cathode of a light-emitting diode 216 of another optoisolator 214 which is also provided between the intermediate circuit 58 and the primary circuit 60. The anode of the light-emitting diode 216 is impressed with an output voltage $V_4$ from the power source 50 through a resistor 218. The output voltage $V_4$ is impressed on the collector of the phototransistor 200 through a resistor 220 and also on one end of each of capacitors 222, 224, respectively connected to the multivibrators 204, 206 through the corresponding resistors 226, 228. One multivibrator 204 concurrently acts as a timer for effecting the changeover of the operation of the light path-switching mirror 48 (FIG. 1). The other multi-vibrator 206 is actuated in response to an output signal from the one multivibrator 204 to generate drive pulses having a short time width.

The primary circuit 60 includes the known autostrobo circuit 230 and a circuit for supplying the flash tube with electric power (hereinafter referred to as "flash tube power supply circuit") 232. In the austrobo circuit 230, a phototransistor 234 is provided in the optoisolator 194 in a state facing the light-emitting diode 196. The emitter and collector of the phototransistor 234 are connected to the input terminals of a thyristor trigger circuit 236 for impressing a firing voltage on the gate of the later described quenching thyristor 252. Another phototransistor 238 is provided in another optoisolator 214 in a state facing the light-emitting diode 216. The emitter and collector of the phototransistor 238 are connected to the corresponding input terminals of a trigger circuit 240. One of the output terminals of the trigger circuit 240 is connected to a trigger coil 242, and the other output terminal of the trigger circuit 240 is connected to the input terminal of a thyristor trigger circuit 243. One of the output terminals of the trigger coil 242 is connected to the trigger circuit 240 and thyristor trigger circuits 236, 243, and further directly to one terminal 66-2 of the primary winding 65 of the second transformer $T_2$ of the power supply circuit 50 (FIG. 2), namely, to a commercial A.C. power source. The other output terminal of the trigger coil 242 is connected to a trigger electrode of the flash tube 46, one end of which is connected to the terminal 66-2 of the primary winding 65 of the second transformer $T_2$ through a resistor 245 and a main thyristor 246. The gate of the main thyristor 246 is connected to the other output terminal of the main thyristor trigger circuit 243. The other end of the flash tube 46 is connected to one end of a parallel circuit of a coil 248 and diode 249, and also to the aforesaid terminal 66-2 of the primary winding 65 of the second transformer $T_2$ through a resistor 250 and a quenching thyristor 252. The gate of the thyristor 252 is connected to the other output terminal of the thyristor trigger circuit 236. A quenching capacitor 254 is connected between the anodes of the thyristors 246, 252. A main capacitor 256 is connected between the terminal 66-2 of the primary winding 65 of the second transformer $T_2$ and the other end of a parallel circuit consisting of the coil 248 and diode 249. Where, therefore, the phototransistor 238 receives an output light signal from the light-emitting diode 216, then the trigger circuit 240 begins to be actuated to impress a firing gate voltage on the gate of the main thyristor 246. At this time, the quenching thyristor trigger circuit 236 starts actuation in response to an output signal from the phototransistor 238 of the optoisolator 194 to impress a firing gate voltage on the gate of a transmission thyristor 252.

The flash tube power supplying circuit 232 is connected to both terminals 66-1, 66-2 of the primary winding 65 of the second transformer $T_2$ of the power supply circuit 50, and further to a commercial A.C. source (not shown). Namely, the input terminal of a charge control circuit 258 is connected to the both terminal 66-1, 66-2 of the primary winding 65 of the second transformer $T_2$. TRIAC 260 is connected in parallel to the charge control circuit 258. One of the terminals of TRIAC 260 is connected to one end of a parallel circuit consisting of the coil 248 and diode 249, that is, the cathode of the diode 249 through three series-connected diodes 262, 263, 264. The cathode of the diode 249 is further connected to the output terminal of the charge control circuit 258. A capacitor 266 is connected in parallel to the diodes 262, 263. A capacitor 268 is connected between the cathode of the diode 262 and said one end 66-2 of the primary winding 65 of the second transformer $T_2$. Therefore, TRIAC 260 connected to the charge control circuit 258 assures the constant voltage charge of the main capacitor 256. The known triple rectifying circuit formed of the diodes 262, 263, 264 and capacitors 266, 268 supplies the main capacitor 256 with a charge voltage three times higher than the commercial A.C. voltage.

Description is now given of the operation of an endoscope light supply device which is the first embodiment of this invention. Where the release button (not shown) of the endoscope camera 34 is depressed, then the shutter 38 is opened, and the synchronizing contact switch 40 is closed. An output signal from the closed switch 40 is transmitted to the patient circuit 56 provided in the control section 54 of the light supply device 20. Accordingly, the optoisolator 106 is driven, and the electromagnet 53 (FIG. 2) is energized. The energized electromagnet 53 lifts the light path-switching mirror 48 (FIG. 1). At this time, the one-shot multivibrator 146 eliminates chattering noises included in an output signal from the closed synchronizing contact switch 40. Thereafter said output signal from the switch 40 is transmitted to the intermediate circuit 58 as a flash tube-actuating signal through the optoisolator 158. This flash tube-actuating signal is delayed by the one-shot multivibrator 204 and converted into a flash tube-actuating pulse signal by another one-shot multivibrator 206. The pulse signal is transmitted to the primary circuit 60 through the optoisolator 214, causing the trigger circuit 240 and main thyristor trigger circuit 243 to be actuated. As a result, an output trigger voltage from the trigger circuit 240 is supplied to the trigger electrode 244 of the flash tube 46. The main thyristor 246 is fired by the main thyristor trigger circuit 243. As a result, the flash tube 46 sends forth a photographic light having a prescribed luminosity.

The photographic light is transmitted straight to the distal end 24 of the light guide 22 through the condenser 49 of FIG. 1, and then illuminates the surface 42 of a patient's coeliac cavity through the light guide 22. A light reflection from the surface 42 enters the beam splitter 30 through the image guide 26. One portion of the light reflection divided by the beam splitter 30 is projected on the film 36 through the eyepiece 32, because the shutter 38 is opened. The other portion of the light reflection divided by the beam splitter 30 enters the optoelectric transducing element 31, an output signal from which is conducted to the patient circuit 56 through the universal cord 18. An output signal from the optoelectric transducing element 31 is amplified by the operation amplifier 114 and then integrated by the integrator 120. Where an output integrated voltage from the integrator 120 reaches a prescribed illumination level or threshold level, then the comparator 128 is actuated to drive the optoisolator 128 is transmitted to the one-shot multivibrator 186 of the intermediate circuit 58 through the optoisolator 140 as a signal for stopping the operation of the flash tube 46. The flash tube-stopping signal is converted into an illumination-stopping pulse by the multivibrator 186, and supplied to the quenching thyristor trigger circuit 236 of the autostrobo circuit 230. Accordingly, the quenching thyristor trigger circuit 236 is actuated to render the quenching thyristor 252 conducting. As a result, the main thyristor 246 is backward biased by the discharge voltage of the quenching capacitor 254, rendering the main thyristor 246 nonconducting. Therefore, the flash tube 46 ceases to be quenched to emit a light.

Where the release button (not shown) of the endoscope camera 34 regains its original position, then the synchronizing contact switch 40 is opened, and the electromagnet 53 is deenergized, causing the light path-switching mirror 48 to return to the normal position.

With the endoscope light supply device of this invention shown in FIGS. 1 to 3, the intermediate circuit 58 is connected between the patient circuit 56 and primary circuit 60. Means of optoisolator is provided not only between the patient circuit 56 and intermediate circuit 58 but also between the intermediate circuit 58 and primary circuit 60, thereby doubly assuring electric insulation. Therefore high voltage impressed between the patient circuit 56 and commercial A.C. power source is split into two levels by one group of optoisolators 140, 158 and another group of optoisolators 194, 214. Where, therefore, a high voltage of, for example, at least 5,000 volts is impressed between the patient circuit 56 and commercial A.C. power source, a voltage impressed on the optoisolators 140, 158, 194, 214 is reduced to about half the original voltage level, that is, about 2,500 volts. Even where, therefore, the conventional optoisolator is applied, the endoscope light supply device of this invention is provided with a sufficiently high insulation property to satisfy the aforementioned safety regulations, and proves completely safe for the human body. Further, the present endoscope light source device eliminates the necessity of applying a pulse transformer, is reduced in manufacturing cost, and is reliably prevented from slowing down in the operation speed.

Figure 4:
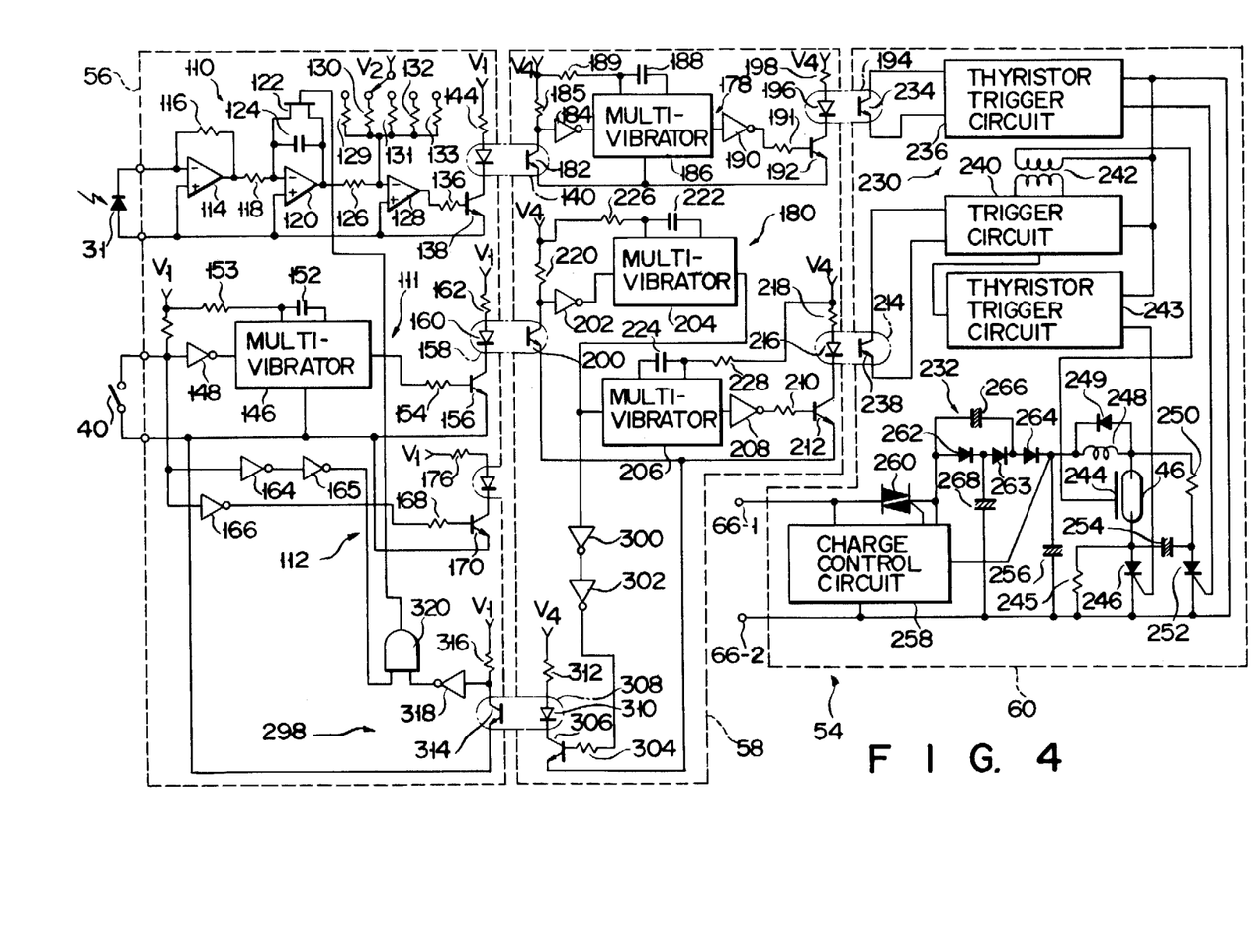
FIG. 4 shows an arrangement of an electric circuit of a control section provided in a second embodiment of this invention.

FIG. 4 shows a second embodiment of the invention. In this embodiment a control circuit 54 is provided with a flash tube control circuit 298. An intermediate circuit 58 has a multivibrator 204, the output terminal of which is connected to the base of an NPN transistor 306 through two inverters 300 and 302 and through a resistor 304. The emitter of the transistor 306 is connected to a point where the emitter of a transistor 212 is connected to the emitter of a phototransistor 200 of an optoisolator 158. The collector of the NPN transistor 306 is connected to the cathode of a photodiode 310 of the optoisolator 158. The anode of the photodiode 310 is connected to receive via a resistor 312 the output voltage $V_4$ of such a power source circuit 50 as shown in FIG. 2.

In the optoisolator 158, a phototransistor 314 is disposed, facing the photodiode 310. The phototransistor 314 is an element of a patient circuit 56. The collector of the phototransistor 314 is connected to receive via a resistor 316 the output voltage $V_1$ of the power source circuit 50. The collector of the phototransistor 314 is connected through an inverter 318 to one of the two input terminals of an AND circuit 320. The other input terminal of the AND circuit 320 is connected to the output terminal of an inverter 165. The output terminal of the AND circuit 320 is connected to the gate of the FET 122. The emitter of the phototransistor 314 is connected to the emitter of a transistor 156.

Except for the above-mentioned features the embodiment of FIG. 4 is the same as that of FIG. 3. Like and the same elements are indicated in FIG. 4 at the same numerals as in FIG. 3, and their functions are not described here.

Now it will be described how the second embodiment operates. With the synchronizing contact switch 40 closed, the multivibrator 204 is started to generate output signals. The output signals of the multivibrator 204 are supplied to said one input terminal of the AND circuit 320 through the optoisolator 308 which is provided between the patient circuit 56 and the intermediate circuit 58. Since the other input terminal of the AND circuit 320 receives an output signal of the synchronizing contact switch 40, the AND circuit 320 is closed. As a result, the output signal of the multivibrator 204 is supplied to the gate of the FET 122. The FET 122 is made nonconductive, whereby the integrator 120 starts operating. In other words, the integrator 120 of the patient circuit 56 is inhibited as long as the multivibrator 204 of the intermediate circuit 58 remains to operate. Hence, the integrator 120 does not unnecessarily operate in response to leaked light into an endoscope 10.

Figure 5:
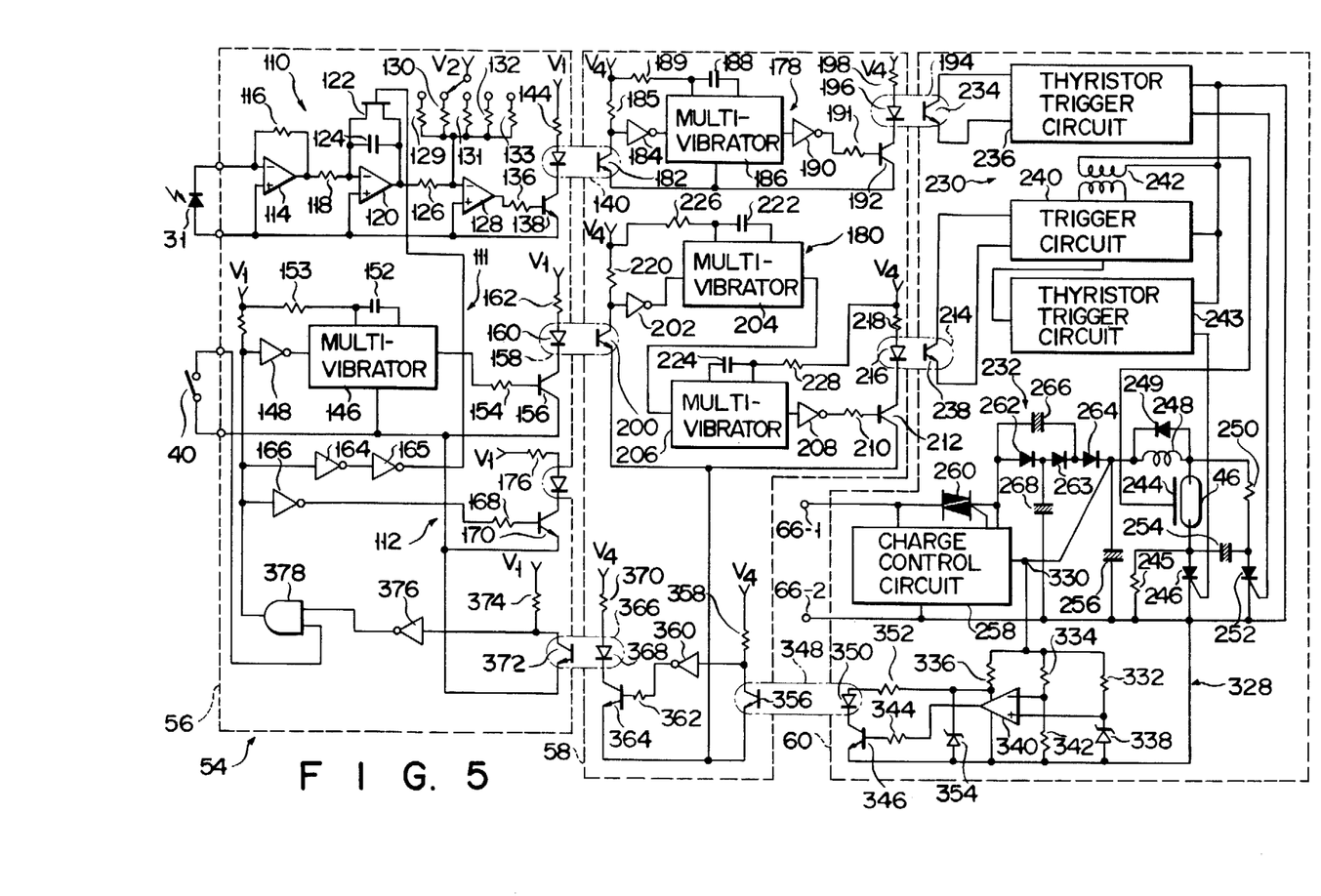
FIG. 5 is an arrangement of an electric circuit of a control section provided in a third embodiment of this invention.
Figure 6:
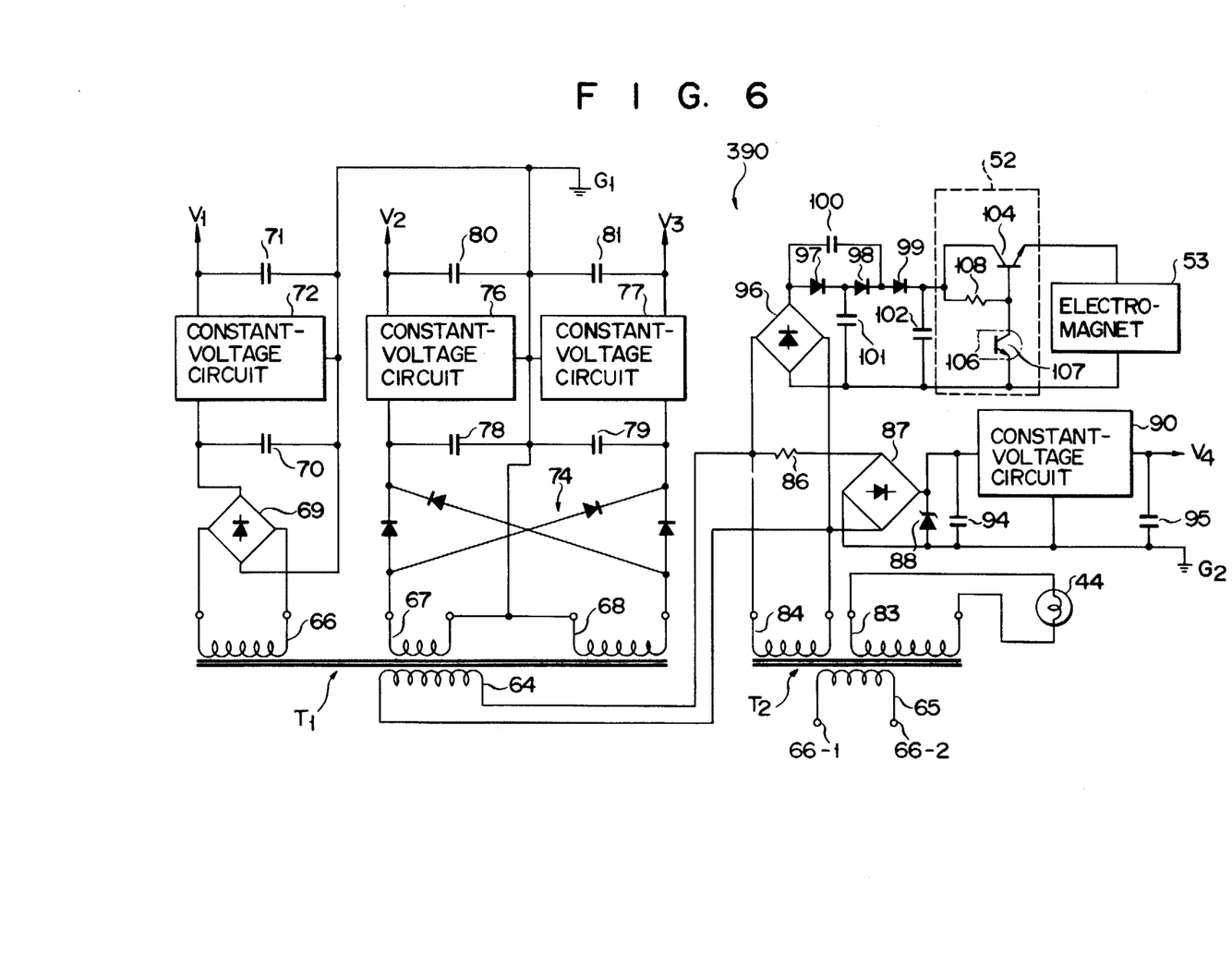
FIG. 6 schematically shows the arrangement of a modification of the electric circuit of FIG. 2.

FIG. 5 shows a third embodiment of the invention. In this embodiment a control circuit 54 is provided with an improper exposure preventing circuit 328. A charge control circuit 258 of a primary circuit 60 has a terminal which is connected to a point where the cathode of a diode 264 is connected to a main capacitor 256. This terminal is connected also to a point where resistors 332, 334 and 336 are connected together. The other end of the resistor 332 is connected via zener diode 338 to a terminal 66-2 of such a second transformer $T_2$ as shown in FIG. 2 and also to the positive input terminal of an operational amplifier 340. The other end of the resistor 334 is connected via a resistor 342 to the terminal 66-2 of the second transformer $T_2$ and also to the negative input terminal of the operational amplifier 340. The output terminal of the operational amplifier 340 is connected to the base of an NPN transistor 346 through a resistor 344. The emitter of this transistor 346 is connected to the terminal 66-2, and the collector thereof is connected to the cathode of a photodiode 350 of an optoisolator 348. The anode of the photodiode 350 is connected to the other end of the resistor 336 through a resistor 352. The other end of the resistor 336 is connected to the terminal 66-2 via a zener diode 354. This structure enables the operational amplifier 340 to receive a bias voltage.

In the optoisolator 348 which connects an intermediate circuit 58 and the primary circuit 60, a phototransistor 356 is disposed, facing the photodiode 350. The collector of the phototransistor 356 is connected to receive the output voltage $V_4$ of such a power supply circuit 50 as shown in FIG. 2. The collector of the phototransistor 356 is connected to the base of an NPN transistor 364 through an inverter 360 and a resistor 362. The emitter of the transistor 364 is connected to the emitter of the phototransistor 356, and the collector thereof is connected to the cathode of a photodiode 368 of an optoisolator 366 which connects a patient circuit 56 and the intermediate circuit 58. The anode of the photodiode 368 is connected to receive via a resistor 370 the output voltage $V_4$ of the power source circuit 50.

In the optoisolator 366 a phototransistor 372 is disposed, facing the photodiode 368. The emitter of the phototransistor 372 is connected to a point where the emitters of NPN transistors 156 and 170 are connected. The collector of the phototransistor 372 is connected to receive the output voltage $V_1$ of the power supply circuit 50. The collector of the phototransistor 372 is connected via an inverter through one of the two input terminals of an AND circuit 378. The other input terminal of the AND circuit 378 is connected to one terminal of a synchronizing contact switch 40. The output terminal of the AND circuit 378 is connected to a point where the input terminals of inverters 148, 164 and 166 are connected.

Except for the above-mentioned features the embodiment of FIG. 5 is the same as that of FIG. 3. Like and the same elements are indicated in FIG. 5 by the same numerals as in FIG. 3, and they are not described here again.

Now it will be described how the third embodiment operates. A reference voltage, which is determined by the zener diode 338, is applied to the positive input terminal of the operational amplifier 340. The main capacitor 256 is charged by the charge control circuit 258. When the capacitor 356 is fully charged, the operational amplifier 340 produces an output signal representing the completion of charging of the capacitor 356. The signal is transmitted to said one input terminal of the AND circuit 278 through the optoisolators 348 and 366, the inverters 360 and 376, etc. Thus, when the synchronizing contact switch 40 is closed, thus supplying a signal to the other input terminal of the AND circuit 278, the output signal of the amplifier 340 is supplied via the AND circuit 278 to the input terminals of the inverters 148, 164 and 166. Consequently, the one-shot multivibrator 146 of the patient circuit 56 starts operating. In other words, the multivibrator 146 remains to generate a signal for actuating the flash tube 46 until the main capacitor 256 is completely charged, even if the synchronizing contact switch 40 is closed. Therefore, it is avoided that the flash tube 46 is actuated before the completion of charging of the capacitor 256, thus applying insufficient light into a body cavity and thus inviting an improper exposure. Although the present invention has been shown and described with respect to particular embodiments, various changes and modifications which are obvious to a person skilled in the art to which the invention pertains are deemed to lie within the spirit, scope and contemplation of the invention. With the embodiment described with reference to FIGS. 1 to 3, a single intermediate circuit 58 is connected between the patient circuit 56 and primary circuit 60. However, it is possible to spatially arrange a plurality of intermediate circuits between the patient circuit 56 and primary circuit 60 with an optoisolator set in the respective spaces. This arrangement enables an endoscope light supply device to have a higher insulation withstand voltage. Even where, therefore, a higher voltage than, for example, 5,000 V is impressed between the patient circuit 56 and primary circuit 60, then an endoscope light supply device can have a greater safety for the human body.

The first transformer $T_1$ of the power supply circuit 50 of FIG. 2 may be connected in the following manner. Namely, with the power supply circuit 390 of FIG. 4, both terminals of the primary winding 64 of the first transformer $T_1$ are connected to both terminals of the secondary winding 84 of the second transformer $T_2$. With this arrangement, therefore, the insulation withstand voltage property between the primary and secondary windings of the first transformer $T_1$ need not to be same as the insulation withstand voltage property between the patient circuit 56 and the primary circuit 60. Thus, the arrangement of the power supply circuit may be more simplified, thereby further reducing the production cost of the subject endoscope light supply device.

What we claim is:

1. A light supply device for an endoscope, comprising:
    a first circuit to be connected to the endoscope;
    a second circuit to be connected to a commercial A.C. power source; and
    a signal transfer means having a plurality of stages of optical coupling means provided between said first and second circuit, for electrically insulating said first and second circuits from each other and for transferring signals between said first and second circuits.

2. A light supply device according to claim 1, wherein said signal transfer means comprises:
    at least one third circuit provided between said first and second circuits for transferring signals between said first and second circuits; and
    a plurality of stages of optical coupling means, at least one of said stages of optical coupling means being provided between said first and third circuits and at least one of said stages of optical coupling means being provided between said second and third circuits.

3. A light supply device according to claim 2, wherein:
    only one third circuit is provided between said first and second circuits; and
    said optical coupling means includes a first stage light coupling section provided between said first circuit and said third circuit, and a second stage light coupling section provided between said second circuit and said third circuit.

4. A light supply device according to claim 3, wherein said first and second light coupling sections each comprise an optoisolator.

5. A light supply device according to claim 2, further comprising a light source connected to said third circuit;
    and wherein:
    said first circuit includes signal-generating circuit means for generating a signal for controlling said light source; and
    said second circuit includes driving circuit means for driving said light source in response to the output signal of said signal-generating circuit means of said first circuit;
    said signal generated by said signal-generating circuit means of said first circuit being supplied to said driving circuit means of said second circuit through said signal transfer means.

6. A light supply device according to claim 5, wherein said light source comprises of a flash tube.

7. A light supply device according to claim 5, wherein said signal-generating circuit means of said first circuit comprises:
    a first signal-generating section including means for receiving a first electrical signal transmitted from the endoscope, and means for removing unnecessary components from the first electrical signal and for producing a signal for actuating said light source from the remainder of the first electrical signal; and
    a second signal-generating section including means for receiving a second electrical signal transmitted from the endoscope, and for producing a signal for stopping the operation of said light source responsive to the second electrical signal.

8. A light supply device according to claim 7, wherein said first stage light coupling section comprises two optoisolators provided between said first and third circuits, said optoisolators respectively corresponding to said first and second signal-generating sections.

9. A light supply device according to claim 5, wherein said second circuit includes circuit means for generating a stop signal for stopping operation of said signal-generating circuit means of said first circuit for a predetermined length of time, said stop signal being transmitted to said first circuit through said signal transfer means.

10. A light supply device according to claim 3, which further comprises:

light-transmitting means for emitting an output light from the light source to the endoscope for a prescribed length of time; and optical coupling means provided between said light-transmitting means said and first circuit to electrically insulate said light-transmitting means and said first circuit from each other and yet optically connect said light-transmitting means and said first circuit together.

11. A light supply device according to claim 10, wherein said light-transmitting means comprises:

means for producing a magnetic flux for a predetermined length of time;

a light path-switching mirror which is disposed close to said magnetic flux-producing means, and, when said magnetic flux-producing means is energized, transmits an output light from said light source to the endoscope; and fourth circuit means connected to said first circuit through said optical coupling means, for driving said magnetic flux-producing means for a prescribed length of time.

12. A light supply device according to claim 11, wherein said first circuit further comprises:

fifth circuit means for generating a signal to operate said magnetic flux-producing means; and means for optically coupling said fourth and fifth circuit means to each other while electrically insulating said fourth and fifth circuit means from each other.

13. A light supply device according to claim 11, wherein said magnetic flux means comprising of an electromagnet.

14. A light supply device according to claim 3, wherein said first stage light coupling section comprises two optoisolators provided between said first and third circuits.

* * * * *